(12) United States Patent
Lin et al.

(10) Patent No.: US 11,246,890 B2
(45) Date of Patent: Feb. 15, 2022

(54) SYSTEMIC TARGETING OF INFLAMMATORY SITES AND ENHANCED IMMUNOMODULATORY FUNCTION BY INTRODUCING THE CHIMERIC ANTIGEN RECEPTOR (CAR) INTO MESENCHYMAL STEM CELLS FOR INFLAMMATORY AND AUTOIMMUNE DISEASES

(71) Applicant: The Board of Trustees of the Leland Stanford Junior University, Stanford, CA (US)

(72) Inventors: Tzuhua Dennis Lin, Palo Alto, CA (US); Stuart B. Goodman, Los Altos, CA (US); Sai-Wen Tang, San Mateo, CA (US); Everett Hurteau Meyer, Belmont, CA (US); Magdiel Pérez Cruz, San Mateo, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 340 days.

(21) Appl. No.: 16/371,371

(22) Filed: Apr. 1, 2019

(65) Prior Publication Data

US 2019/0298774 A1 Oct. 3, 2019

Related U.S. Application Data (60) Provisional application No. 62/652,176, filed on Apr. 3, 2018.

(51) Int. Cl.
| | |
|---|---|
| *A61K 35/28* | (2015.01) |
| *A61K 47/68* | (2017.01) |
| *A61P 3/10* | (2006.01) |
| *A61K 39/00* | (2006.01) |
| *C07K 14/54* | (2006.01) |
| *C07K 16/28* | (2006.01) |

(52) U.S. Cl.
CPC .......... *A61K 35/28* (2013.01); *A61K 47/6849* (2017.08); *A61P 3/10* (2018.01); *C07K 14/5406* (2013.01); *C07K 16/28* (2013.01); *A61K 2039/5156* (2013.01)

(58) Field of Classification Search
CPC .............. A61K 35/28; A61K 47/6849; A61K 2039/5156; C07K 16/28; C07K 2319/03; C07K 2319/33; C12N 2510/00
See application file for complete search history.

(56) References Cited

U.S. PATENT DOCUMENTS

| | | | | |
|---|---|---|---|---|
| 2014/0286973 | A1* | 9/2014 | Powell, Jr. ............. | C07K 16/28 424/185.1 |
| 2016/0237407 | A1* | 8/2016 | Wagner ............... | C07K 14/7051 |
| 2016/0272718 | A1 | 9/2016 | Wang et al. | |
| 2017/0218337 | A1 | 8/2017 | Friedman | |
| 2017/0274095 | A1 | 9/2017 | Meyer et al. | |
| 2018/0044424 | A1 | 2/2018 | June | |
| 2019/0167725 | A1* | 6/2019 | Park ....................... | A61P 37/06 |

FOREIGN PATENT DOCUMENTS

| | | |
|---|---|---|
| CN | 104845933 A | 8/2015 |
| WO | 2010119039 A1 | 10/2010 |
| WO | 2017058752 A1 | 4/2017 |

OTHER PUBLICATIONS

Bhatt et al. (2014) "Regulation of the NF-kB-mediated transcription of inflammatory genes" Immunology 5:71 1-9.
Lu et al. (2017) Mesenchymal stem cells for treating autoimmune dacryoadenitis. Stem Cell Research & Therapy 8:1 126.
Lynn et al. (2015) "Targeting of folate receptor beta on acute myeloid leukemia blasts with chimeric antigen receptor expressing T cells" Blood., vol. 125(22): 3466-76.
Payne et al. (2012) "Early intervention with gene modified mesenchymal stem cells overexpressing interleukin-4 enhances anti-inflammatory responses and functional recovery in experimental autoimmune demyelination" Cell Adhesion & Migration 6:3 179-189.
Tang et al. (2015) "Therapeutic potential of CAR-T cell-derived exosomes: a cell-free modality for targeted cancer therapy" Oncotarget 6:42 44179-44190.

\* cited by examiner

*Primary Examiner* — Daniel C Gamett
(74) *Attorney, Agent, or Firm* — Pamela J. Sherwood; Bozicevic, Field & Francis LLP (57) ABSTRACT

Mesenchymal stromal cells are engineered to express a chimeric antigen receptor (CAR), that specifically binds a marker of activated myeloid cells, including without limitation folate receptor beta; and are administered to an individual for treatment of inflammation at sites characterized by the presence of activated myeloid cells.

12 Claims, 5 Drawing Sheets
(3 of 5 Drawing Sheet(s) Filed in Color)

SYSTEMIC TARGETING OF INFLAMMATORY SITES AND ENHANCED IMMUNOMODULATORY FUNCTION BY INTRODUCING THE CHIMERIC ANTIGEN RECEPTOR (CAR) INTO MESENCHYMAL STEM CELLS FOR INFLAMMATORY AND AUTOIMMUNE DISEASES

CROSS REFERENCE

This application claims benefit of U.S. Provisional Patent Application No. 62/652,176, filed Apr. 3, 2018, which applications are incorporated herein by reference in their entirety.

BACKGROUND OF THE INVENTION

Mesenchymal stem cells (MSCs) are an attractive source of cells for cell-based therapy in inflammatory diseases because of their immunomodulatory properties, low immunogenicity and tissue repair properties. They have been shown to alleviate tissue injury and promote tissue repair in autoimmune disease. In addition, extensive in vitro studies have shown that MSCs can prevent entry of T lymphocytes into the cell cycle, thus preventing the clonal expansion of activated lymphocytes necessary for an effective immune response.

The last decade has seen much progress in adjunctive cell therapy for immune disorders. For example, Phase III clinical trials have been run using mesenchymal stromal cells (MSC) for treatment of Graft versus Host Disease (GvHD), and product approval has been achieved for treatment of pediatric GvHD in Canada and New Zealand (Prochymal (®); Osiris Therapeutics). This effectiveness has prompted the prophylactic use of adherent stem cells at the time of allogeneic hematopoietic stem cell transplantation (HSCT) to prevent occurrence of GvHD and possibly provide stromal support for hematopoietic recovery. The MultiStem (®) product is an adult adherent stem cell product derived from bone marrow.

In addition to effects on T lymphocytes, MSCs also alter cytokine secretion by mature dendritic cells, prevent differentiation of monocytes into dendritic cells and prevent upregulation of CD1a, CD40, CD80, CD86 and HLA-DR upon activation. Monocytes cultured in the presence of MSCs fail to enter the cell cycle upon exposure to granulocyte-macrophage colony-stimulating factor (GM-CSF) and IL-4, an effect attributed to downregulation of cyclin D2 in the cultured monocytes. MSCs appear to require priming by a combination of IFN-γ and one of TNF-α, IL-1α or IL-1β to exert these effects, suggesting that there is important bidirectional cross-talk between immune cells and the local microenvironment. The mediators responsible for the immunomodulatory effects of MSCs may include nitric oxide. Other immunomodulatory mechanisms proposed for these cells include tryptophan degradation by indoleamine-2,3-dioxygenase, prostaglandin E2, soluble HLA-G and polarization of APCs to more tolerogenic phenotypes.

There is a need for methods and compositions for sensing inflammatory environments and secreting physiological levels of anti-inflammatory cytokines in response. The present invention addresses this issue.

SUMMARY OF THE INVENTION

Compositions and methods are provided for treating inflammatory disease in an individual by targeting mesenchymal stromal cells (MSC) to sites where activated myeloid cells, particularly macrophages, are present. Engineered MSC are provided for administration to the individual; which MSC express a chimeric antigen receptor (CAR) that binds to an antigen specifically present on activated myeloid cells. In some embodiments the antigen present on activated myeloid cells is folate receptor beta (FRβ). The CAR provides localization of the MSC at the sites where activated myeloid cells are present.

In some embodiments the MSC are also genetically engineered to express a cytokine. In some embodiments the cytokine induces an M2 phenotype in macrophages, e.g. an anti-inflammatory cytokine. In some embodiments the cytokine is IL-4. In some embodiments the cytokine is IL-13. In some such embodiments the cytokine expression is coordinately regulated to be expressed with the chimeric antigen receptor, including without limitation expression of a fusion protein of the CAR and cytokine linked by a cleavable peptide, e.g. cleavable 2A peptide. In other embodiments the cytokine is constitutively expressed; or is regulated separately from the CAR construct, e.g. regulated by NF-κB. The construct can be introduced into the MSC via viral vector, by transfection of mRNA, etc. Because the anti-inflammatory cytokine secreted by the engineered MSC can re-program local inflammatory M1 macrophages into M2 phenotype, MSCs engineered as disclosed herein can also be targeted to tissues for methods of enhancing tissue regeneration, e.g., fracture healing, wound healing, tissue repair.

Engineered MSC comprising a CAR that recognizes FRβ may bind to FRβ directly or indirectly. Indirect binding systems utilize a CAR, which may be referred to as iCAR, that comprises as a targeting moiety an scFv that specifically binds to a non-endogenous antigenic moiety. In some embodiments, the antigenic moiety is a small molecule, e.g. a hapten, including without limitation fluorescein isothiocyanate (FITC), streptavidin, biotin, dinitrophenol, phycoerythrin (PE), and the like. Fluorescein isothiocyanate (FITC) is exemplary. An antibody conjugated to the non-endogenous antigenic moiety is administered to the individual in combination with the engineered MSC, where the iCAR binds to the antibodies, which are bound to FRβ expressed by activated myeloid cells. In the direct binding embodiment, the CAR comprises an scFv specific for FRβ, and thereby directly binds to the activated myeloid cells.

The MSC may be autologous or allogeneic with respect to the recipient. In some embodiments, MSC are pooled allogeneic cells, e.g. obtained from bone marrow, adipose tissue, etc., and may be commercially available preparations. In other embodiments MSC are isolated from patient tissue, e.g. bone marrow, adipose tissue, etc. MSC can be purified by culture and/or by selection for suitable cell surface markers. In some embodiments, the cells are expanded in culture following introduction of the CAR genetic construct.

The engineered MSC are administered to an individual suffering from an inflammatory condition. For the indirect binding embodiment, the engineered cells are administered in combination with administration of the folate receptor targeting antibodies. By localizing MSC at the site of inflammation, the effectiveness of the MSC is enhanced. The effectiveness of the MSC may be further enhanced by delivery of a cytokine, including without limitation IL-4, IL-13, etc.

Targeted MSC are effective non-toxic modalities for the treatment of inflammatory conditions in which activated monocytic cells are involved. Patients with a variety of inflammatory disorders, including rheumatoid arthritis, Crohn's disease, ischemic bowel disease, Sjogren's syndrome, localized infections, atherosclerosis, and organ transplant rejection show FRβ expression at inflammatory sites. In some embodiments of the invention, the engineered MSC are administered to the individual for treatment of a diabetic condition, including insulin resistance, metabolic syndrome, obesity, Type 2 diabetes, insulin dependent diabetes mellitus (IDDM), etc. In some embodiments the engineered MSC are administered to an individual in conjunction with pancreatic islet transplantation. In some embodiments the engineered MSC are administered to an individual for treatment of inflammatory-associated diseases including bone regeneration, osteoarthritis, myocardial infarction, diabetes, pulmonary hypertension, inflammatory bowel disease, spinal cord injury, etc.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1B. Diagram of constituent parts of interposed CAR-MSC approach.

FIG. 5. IL4 secretion by the iCAR-MSC. Six million of iCAR-MSC and the mock-transfected control were seeded into T175 culture flasks after electroporation. The supernatant was collected at day 1, 2, 3, and 6 post-electroporation, and the IL4 level was quantified by ELISA (eBioscience).

FIG. 6. Macrophage polarization by the conditioned medium from iCAR-MSC. Macrophages were treated with the supernatant collected from iCAR-MSC and the mock-transfected control at indicated time points. Cellular RNA has harvested 24 hrs after treatment with the supernatant with or without 100 ng/ml LPS (M1 stimulator). The expression of anti-inflammatory (M2, Arginase 1/CD206) and pro-inflammatory (M1, TNFα/iNOS) markers was determined by quantitative PCR using Taqman system (Applied Biosystems).

DETAILED DESCRIPTION OF THE EMBODIMENTS

The present invention provides engineered MSC that express a chimeric antigen receptor (iCAR) that binds to and is activated by targeting monoclonal antibodies, including without limitation binding to a small molecule tag present on the targeting antibodies. The MSC are targeted to sites where activated myeloid cells, particularly macrophages, are present. The MSC may be further engineered to express a cytokine that induce macrophages to an M2 phenotype.

Definitions

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

General methods in molecular and cellular biochemistry can be found in such standard textbooks as Molecular Cloning: A Laboratory Manual, 3rd Ed. (Sambrook et al., CSH Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

Mesenchymal Stem Cell (MSC). The term "mesenchymal stem cell" or "mesenchymal stromal cell" has traditionally been applied to encompass many of progenitor cell classes including stromal cells derived from bone marrow, adipose tissue, and other organs. MSC have utility in the field of transplantation and immunotherapy with respect to hematopoietic support, immunoregulation, graft facilitation, and gene therapy. An important role in immunoregulation is supported by reports that these cells can suppress T cell activation without inducing allogeneic anergy. These findings may have important applications for stem cell transplantation, organ transplantation, and other regenerative and reparative therapies.

When referring to human MSCs, the term refers to those cells that meet the minimal criteria to define human MSCs as proposed by the Mesenchymal and Tissue Stem Cell Committee of the International Society for Cellular Therapy (ISCT): (1) MSCs are plastic-adherent when maintained in standard culture conditions; (2) MSCs express CD105, CD73, and CD90 and lack expression of CD45, CD34, CD14 or CD11b, CD79a or CD19, and HLA-DR surface molecules; and (3) MSCs differentiate into osteoblasts, adipocytes, and chondroblasts in vitro (e.g., see Dominici et al., Cytotherapy. 2006; 8(4):315-7). Additional functional criteria may include, without limitation, expression of TNF receptor 1 [TNFR1] and responsiveness to TNF; and inhibition of IL-2 receptor alpha [IL-2-RA] expression by activated T lymphocytes.

It will be understood by those of skill in the art that expression levels reflect detectable amounts of the marker (e.g., nucleic acid or protein) on and/or in the cell. A cell that is negative for staining (e.g., the level of binding of a marker specific reagent is not detectably different from a matched control) may still express minor amounts of the marker. And while it is commonplace in the art to refer to cells as "positive" or "negative" for a particular marker, actual expression levels are quantitative traits. The number of detected molecules can vary by several logs, yet still be characterized as "positive".

When a protein marker is used, the staining intensity (e.g., of a marker-specific antibody) can be monitored by flow cytometry, where lasers detect the quantitative levels of fluorochrome (which is proportional to the amount of cell marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell can be recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining brighter than that of an isotype matched control, but is not as intense as the most brightly staining cells normally found in the population. An alternative control may utilize a substrate having a defined density of marker on its surface, for example a fabricated bead or cell line, which can provide the positive control for intensity.

MSC are found in bone marrow, and have also been harvested from the supportive stroma of a variety of tissues. MSCs can be isolated from a number of sources and cells from any convenient source can be used. MSCs have been isolated from adipose tissue, peripheral blood, umbilical cord blood, amniotic fluid, skin, dental pulp, synovium, umbilical cord tissue, placental complex, tendon, gut, muscle, cartilage, and endometrium. Some evidence suggests that MSCs may be present virtually in any vascularized tissue throughout the whole body (e.g., see Arutyunyan et. al., Stem Cells Int. 2016; 2016:6901286; Prockop, Science. 1997 Apr. 4; 276(5309):71-4; and Tuan et. al., Arthritis Res Ther. 2003; 5(1):32-45). An MSC isolated from any source, including those listed above, can be used in the compositions and methods of this disclosure. In both mouse and human a population of cells has been identified in subcutaneous adipose tissue (AMSC). These cells have demonstrated the same in vitro differentiation capacity as BM-MSC for the mesenchymal lineages, osteoblasts, chondrocytes, myocytes, neurons, and adipocytes (Zuk et al. (2002) Mol Biol Cell 13, 4279-95; Fujimura et al. (2005) Biochem Biophys Res Commun 333, 116-21).

Among commercially available sources, Remestemcel-L is a cellular therapy product marketed under the trade name Prochymal® by Osiris Therapeutics. Remestemcel-L consists of cultured, cryopreserved MSCs derived from the bone marrow of healthy donors. Although the production is proprietary, donors are screened and tested according to FDA guidelines for Blood and Tissue Based Products. Cells from the final culture and in-production lots are tested for safety (absence of contaminating viruses, bacteria and fungi), purity (absence of hematopoietic cells), identity (expression of such appropriate MSC markers as CD105, CD73, CD90), potency (expression of TNF receptor 1 [TNFR1] and inhibition of IL-2 receptor alpha [IL-2-RA] expression by activated T lymphocytes) and viability. Remestemcel-L may be thawed and diluted with PlasmaLyte A prior to use.

Alternatively, a convenient source for MSC are adipose-derived cells. By "adipose" is meant any fat tissue. The adipose tissue may be brown or white adipose tissue, derived from subcutaneous, omental/visceral, mammary, gonadal, or other adipose tissue site. Preferably, the adipose is subcutaneous white adipose tissue. The adipose tissue may be from any organism having fat tissue. Preferably, the adipose tissue is mammalian, most preferably the adipose tissue is human. A convenient source of adipose tissue is from liposuction surgery, however, the source of adipose tissue or the method of isolation of adipose tissue is not critical to the invention. Methods for the isolation, expansion, and differentiation of human adipose tissue-derived cells have been reported. See for example, Burris et al 1999, Mol Endocrinol 13:410-7; Erickson et al 2002, Biochem Biophys Res Commun. Jan. 18, 2002; 290(2):763-9; Gronthos et al 2001, Journal of Cellular Physiology, 189:54-63; Halvorsen et al 2001, Metabolism 50:407-413; Halvorsen et al 2001, Tissue Eng. 7(6):729-41; Harp et al 2001, Biochem Biophys Res Commun 281:907-912; Saladin et al 1999, Cell Growth & Diff 10:43-48; Sen et al 2001, Journal of Cellular Biochemistry 81:312-319; Zhou et al 1999, Biotechnol. Techniques 13: 513-517. Adipose tissue-derived stromal cells may be obtained from minced human adipose tissue by collagenase digestion and differential centrifugation [Halvorsen et al 2001, Metabolism 50:407-413; Hauner et al 1989, J Clin Invest 84:1663-1670; Rodbell et al 1966, J Biol Chem 241:130-139].

For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Cells may be purified by culture to select for adherent stromal cells using established protocols, and may further be selected for phenotypic markers. Various ways to isolate MSCs are known in the art and any convenient method can be used. For example, one protocol for isolating MSCs from mouse compact bone includes flushing bone marrow out of long bones, digesting the bone chips with collagenase type II, deprivation of the released cells, and culturing the digested bone fragments, out of which fibroblast-like cells migrate and grow in the defined medium. MSCs are also commercially available. For additional information related to MSCs and various ways to isolate them, see, e.g., Zhu et. al., "A protocol for isolation and culture of mesenchymal stem cells from mouse compact bone" Nat Protoc. 2010 March; 5(3):550-60; Lin et. al., J Orthop Res. 2016 Apr. 22; Gibon et. al., Stem Cell Res Ther. 2016 Mar. 22; 7:44; Loi et. al., Bone. 2016 May; 86:119-30. doi: 10.1016/j.bone.2016.02.020; Yao et. al., J Biomed Mater Res A. 2016 September; 102(9):3291-7; xx et. al., J Biomed Mater Res A. 2013 July; 101(7):2067-74; Gibon et. al., Biomaterials. 2012 May; 33(14):3632-8; Pittenger et. al., Science. 1999 Apr. 2; 284(5411):143-7; Arutyunyan et. al., Stem Cells Int. 2016; 2016:6901286; Noth et. al., J Orthop Res. 2002 September; 20(5):1060-9; Watson et. al., Stem Cell Res Ther. 2014 Apr. 15; 5(2):51, Lee et. al., Tissue Eng Part C Methods. 2016 Sep. 28; Li et. al., Ann N Y Acad Sci. 2016 April; 1370(1): 109-18; and Caterson et. al., Mol Biotechnol. 2002 March; 20(3):245-56; as well as U.S. Pat. Nos. 9,456,893; 9,458, 429; 9,457,051; 9,434,925; and 9,421,304, all of which are hereby incorporated by reference in their entirety.

Cells isolated from tissues may be used immediately. Alternatively, the cell population may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human.

The cells which are employed may be fresh, frozen, or have been subject to prior culture. They may be fetal, neonate, adult. MSC may be obtained from adipose tissue (see U.S. Patent application 20030082152); bone marrow (Pittenger et al. (1999) Science 284(5411):143-147; Liechty et al. (2000) Nature Medicine 6:1282-1286); G-CSF or GM-CSF mobilized peripheral blood (Tondreau et al. (2005) Stem Cells 23(8): 1105-1112), or any other conventional source, including commercially available cells.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

The term "genetic modification" means any process that adds, deletes, alters, or disrupts an endogenous nucleotide sequence and includes, but is not limited to viral mediated gene transfer, liposome mediated transfer, transformation, transfection and transduction, e.g., viral mediated gene transfer such as the use of vectors based on DNA viruses such as lentivirus, adenovirus, retroviruses, adeno-associated virus and herpes virus. Also included are methods of engineering using, for example CRISPR/CAS9 systems for modification.

"Variant" refers to polypeptides having amino acid sequences that differ to some extent from a native sequence polypeptide. Ordinarily, amino acid sequence variants will possess at least about 80% sequence identity, more preferably, at least about 90% homologous by sequence. The amino acid sequence variants may possess substitutions, deletions, and/or insertions at certain positions within the reference amino acid sequence.

A "cytokine" is a protein released by one cell to act on another cell as an intercellular mediator. Cytokine of interest include, without limitation, those cytokines that promote an M2 phenotype in macrophages. Specific cytokines may include IL-4, and IL-13.

Human IL4 is an 18-kD glycoprotein (Yokota et al. (1986) *P.N.A.S.* 83:5894-5898). It is a pleiotropic cytokine, produced by activated T cells and other cells. This cytokine is a ligand for interleukin 4 receptor. The interleukin 4 receptor also binds to IL13, which may contribute to many overlapping functions of this cytokine and IL13. STATE, a signal transducer and activator of transcription, has been shown to play a central role in mediating the immune regulatory signal of this cytokine. Two alternatively spliced transcript variants of this gene encoding distinct isoforms have been reported. The reference sequence for human IL-4 may be accessed at Genbank, NP_000580.

Interleukin 13 (IL-13) is a protein that in humans is encoded by the IL13 gene. It is located on chromosome 5q31 with a length of 1.4 kb. The protein is 13 kDa and folds into 4 alpha helical bundles. The secondary structural features of IL-13 are similar to that of Interleukin 4 (IL-4); however it only has 25% sequence homology to IL-4 and it's capable of IL-4 independent signaling. The reference sequence for human IL-13 protein may be accessed at Genbank, NP_002179.

The cytokine coding sequences may be least about 50 amino acids in length, at least about 75, at least about 100, at least about 110, at least about 115 amino acids in length, up to the full-length of the wild-type protein at the transmembrane domain, and are optionally fused to a heterologous polypeptide or conjugated to a carrier molecule such as PEG, etc. In some embodiments the cytokine is fused to the CAR coding sequence through a cleavable linker peptide.

The term "gene" means the segment of DNA involved in producing a polypeptide chain; it includes regions preceding and following the coding region "leader and trailer" as well as intervening sequences (introns) between individual coding segments (exons). Some genes may be developed which lack, in whole or in part, introns. Some leader sequences may enhance translation of the nucleic acid into polypeptides.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

Chimeric Antigen Receptor (CAR). The CAR architecture may be any suitable architecture, as known in the art and as illustrated in FIG. 1, comprising an antigen binding domain and a transmembrane domain. The antigen recognition domain is typically derived from an scFv that selectively binds to the non-endogenous antigenic moiety. For the purposes of the present invention, a typical CAR architecture with a cytoplasmic signaling domain is not required. The transmembrane domain may be linked to the cytokine coding sequence through a cleavable peptide.

Spacer. A spacer region may link the antigen binding domain to the transmembrane domain. It should be flexible enough to allow the antigen binding domain to orient in different directions to facilitate antigen recognition. The simplest form is the hinge region from an immunoglobulin, e.g. the hinge from any one of IgG1, IgG2a, IgG2b, IgG3, IgG4, particularly the human protein sequences. Alternatives include the $CH_2CH_3$ region of immunoglobulin and portions of CD3. For many scFv based constructs, an IgG hinge is effective.

Linker peptide. A T2A or P2A peptide can be used to link the CAR to an epitope tag or other protein or peptide, including without limitation a sortable tag, IL-4, IL-13, etc.

T2A or P2A-linked multicistronic vectors can be used to express multiple proteins from a single open reading frame. The small cleavable peptide sequences, when cloned between genes, allow for efficient, stoichiometric production of discrete protein products within a single vector through a novel "cleavage" event within the cleavable peptide sequence. Various cleavable peptide sequences are known and used in the art, for example see Szymczak-Workman et al. (2012) Cold Spring Harb Protoc. 2012(2):199-204, herein specifically incorporated by reference. They are small (18-22 amino acids) and have divergent amino-terminal sequences, which minimizes the chance for homologous recombination and allows for multiple, different 2A peptide sequences to be used within a single vector.

Folate receptor beta (FOLR2, FRβ) is a member of the folate receptor family. Members of this gene family have a high affinity for folic acid and for several reduced folic acid derivatives, and they mediate delivery of 5-methyltetrahydrofolate to the interior of cells. This protein has a 68% and 79% sequence homology with the FOLR1 and FOLR3 proteins, respectively.

In monocytes and macrophage-lineage cells, also referred to herein as myeloid cells, FRβ expression is increased upon activation, i.e. in activated myeloid cells. The β isoform of the FR is primarily, if not exclusively, expressed on the monocyte subpopulation of human peripheral blood cells. FR-β⁺ peripheral blood cells belong almost exclusively to a proinflammatory subpopulation of monocytes, although not all proinflammatory monocytes express FR-β. For example, FRβ is expressed and functional in synovial macrophages in rheumatoid arthritis patients. Patients with a variety of inflammatory disorders, including rheumatoid arthritis, Crohn's disease, ischemic bowel disease, Sjogren's syndrome, localized infections, atherosclerosis, and organ transplant rejection show uptake of a folate at sites of inflammation (see Low et al., Acc Chem Res. 41(1):120-9 (2008); Matteson et al., Clin Exp Rheumatol 27:253-259 (2009); and Ayala-Lopez et al., J Nuc Med, 51:768-774 (2010)). These findings indicate expression of FRβ in activated macrophages and monocytes.

Macrophages are highly adaptive myeloid cells that respond to environmental stimuli and differentiate into a diversity of subsets with both pro- and anti-inflammatory properties. Although macrophages display a true continuum of phenotypes in vivo, for simplicity, these phenotypes have often been categorized into classically activated macrophages (CAMs or M1) and alternatively activated macrophages (AAMs or M2). CAMs have been linked to the development of autoimmune diseases, such as RA, diabetes, psoriasis, and Crohn's disease, AAMs have been more closely tied to tumor progression, certain allergies, and various forms of fibrosis. Based on their prominent contributions to these pathologies, activated macrophages have become a prime target for treatment of many autoimmune and inflammatory diseases.

Antibodies that specifically bind to FRβ are known in the art, or can be generated using art-recognized methods. For example, functional recombinant human FRβ protein was produced in insect cells and used as antigen to isolate the antibody m909, from a human naïve Fab phage display library. See, for example, Feng et al. Arthritis Res Ther. 2011; 13(2):R59. The anti-human FRβ antibody 94b/FOLR2 is described by Nagayoshi et al. 2005. Arthritis Rheum. 9:2666. Additional anti-human folate receptor beta antibodies and methods of use are described in U.S. Pat. No. 8,871,206; each of which are herein specifically incorporated by reference. For analysis in an animal model, for example a mouse model, antibodies specific for the mouse FRβ may find use, e.g. the CL10 antibody.

Targeting antibody. A targeting antibody specifically binds to the targeting antigen found in the region (or lesion) of the undesirable inflammation, i.e. folate receptor R. A targeting antibody is typically modified by conjugation to a non-endogenous antigenic moiety.

Non-endogenous antigenic moiety. A non-endogenous antigenic moiety is an antigen not normally present in the body. Typically, the moiety is of a sufficiently small size that it can be used as a label, or tag, on a monoclonal antibody, but is of a size sufficient to bind to the iCAR protein.

In some embodiments, the antigenic moiety is a small molecule, e.g. a hapten, including without limitation fluorescein isothiocyanate (FITC), streptavidin, biotin, dinitrophenol, phycoerythrin (PE), green fluorescent protein, horseradish peroxidase, histidine, streptavidin, fluorescent tags, and the like.

The antigenic moiety may be conjugated to the targeting antibodies using techniques such as chemical coupling and chemical cross-linkers. Alternatively, polynucleotide vectors can be prepared that encode the targeting antibodies as fusion proteins.

Antibody: As used herein, the term "antibody" refers to a polypeptide that includes canonical immunoglobulin sequence elements sufficient to confer specific binding to a particular target antigen. As is known in the art, intact antibodies produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure.

The term antibody includes genetically engineered or otherwise modified forms of immunoglobulins, such as intrabodies, peptibodies, chimeric antibodies, fully human antibodies, humanized antibodies, and heteroconjugate antibodies (e.g., bispecific antibodies, diabodies, triabodies, and tetrabodies). The term functional antibody fragment includes antigen binding fragments of antibodies, including e.g., Fab', F(ab')$_2$, Fab, Fv, rIgG, and scFv fragments. The term scFv refers to a single chain Fv antibody in which the variable domains of the heavy chain and of the light chain of a traditional two chain antibody have been joined to form one chain.

The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation.

Any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, antibody sequence elements are humanized, primatized, chimeric, etc, as is known in the art.

The use of a single chain variable fragment (scFv) is of particular interest for developing a CAR construct. scFvs are recombinant molecules in which the variable regions of light and heavy immunoglobulin chains encoding antigen-binding domains are engineered into a single polypeptide. Generally, the $V_H$ and $V_L$ sequences are joined by a linker sequence. See, for example, Ahmad (2012) Clinical and Developmental Immunology Article ID 980250, herein specifically incorporated by reference.

Sequences encoding the CAR and cytokine can be introduced into the MSC as mRNA, on a vector, integrated into the MSC genome, etc.

As used herein, a "vector" may be any agent capable of delivering or maintaining nucleic acid in a host cell, and includes viral vectors (e.g. retroviral vectors, lentiviral vectors, adenoviral vectors, or adeno-associated viral vectors), plasmids, naked nucleic acids, nucleic acids complexed with polypeptide or other molecules and nucleic acids immobilized onto solid phase particles. The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art. Transcription of the DNA encoding the polypeptides of the present invention by higher eukaryotes is increased by inserting an enhancer sequence into the vector. Enhancers are cis-acting elements of DNA, usually about from 10 to 300 by that act on a promoter to increase its transcription. Examples including the SV40 enhancer on the late side of the replication origin by 100 to 270, a cytomegalovirus early promoter enhancer, the polyoma enhancer on the late side of the replication origin, and adenovirus enhancers.

An "expression cassette" comprises a DNA coding sequence (e.g., a nucleotide sequence encoding a polypeptide such as an anti-inflammatory cytokine) operably linked to a transcriptional control element. "Operably linked" refers to a juxtaposition wherein the components so described are in a relationship permitting them to function in their intended manner. For instance, a control element is operably linked to a coding sequence (and likewise the coding sequence is operably linked to the control element) if the control element affects transcription/expression of the coding sequence. As would be readily understood by one of ordinary skill in the art, a nucleotide sequence can be operably linked to more than one control element (e.g., a promoter and a NFκB inflammation response element).

The terms "recombinant expression vector," "expression vector" and similar terms of the art are used interchangeably herein to refer to a DNA molecule comprising a vector and at least one insert, where the insert includes an expression cassette (e.g., an NFκB inflammation response element operably linked to a nucleotide sequence encoding a cytokine). Recombinant expression vectors can be generated for the purpose of expressing and/or propagating the insert(s) (e.g., in bacteria), or for the construction of other recombinant nucleotide sequences. In some cases, a subject nucleic acid (e.g., an expression cassette, an expression vector, a viral expression vector, a linear expression vector, a circular expression vector, a plasmid, and the like) includes an NFκB inflammation response element operably linked to a nucleotide sequence encoding a cytokine (e.g., IL-4, IL-6, IL-10, IL-11, or IL-13), etc.

Suitable expression vectors include, but are not limited to, viral vectors (e.g., viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166: 154-165; and Flotte et al., PNAS (1993) 90:10613-10617); SV40; herpes simplex virus; human immunodeficiency virus (HIV) (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); lentiviral vector (e.g., a CD511B-1 lentiviral expression vector modified to include an NFκB inflammation response element operably linked to a nucleotide sequence encoding an anti-inflammatory cytokine); and the like.

Numerous suitable expression vectors are known to those of skill in the art, and many are commercially available. The following vectors are provided by way of example as vectors that can be modified to include an NFκB inflammation response element operably linked to a nucleotide sequence encoding an anti-inflammatory cytokine: pXT1, pSG5 (Stratagene), pSVK3, pBPV, pMSG, pCMV3, pGL4.32 [luc2/NF-κB-RE/Hygro], and pSVLSV40 (Pharmacia). However, any convenient vector can be used and many suitable vectors will be known to one of ordinary skill in the art.

Inflammatory Disease. Inflammation is a process whereby the immune system responds to infection or tissue damage. Inflammatory disease results from an activation of the immune system that causes illness, in the absence of infection or tissue damage, or at a response level that causes illness. Inflammatory disease includes autoimmune disease, which are any disease caused by immunity that becomes misdirected at healthy cells and/or tissues of the body. Autoimmune diseases are characterized by T and B lymphocytes that aberrantly target self-proteins, -polypeptides, -peptides, and/or other self-molecules causing injury and or malfunction of an organ, tissue, or cell-type within the body (for example, pancreas, brain, thyroid or gastrointestinal tract) to cause the clinical manifestations of the disease. Autoimmune diseases include diseases that affect specific tissues as well as diseases that can affect multiple tissues, which can depend, in part on whether the responses are directed to an antigen confined to a particular tissue or to an antigen that is widely distributed in the body.

The immune system employs a highly complex mechanism designed to generate responses to protect mammals against a variety of foreign pathogens while at the same time preventing responses against self-antigens. In addition to deciding whether to respond (antigen specificity), the immune system must also choose appropriate effector functions to deal with each pathogen (effector specificity). An intermediary cell critical in regulating these effector functions are macrophages and other myeloid cells.

Included in inflammatory disease is diabetes, which is a metabolic disease that occurs when the pancreas does not produce enough of the hormone insulin to regulate blood sugar ("type 1 diabetes mellitus") or, alternatively, when the body cannot effectively use the insulin it produces ("type 2 diabetes mellitus").

According to recent estimates by the World Health Organization, more than 200 million people worldwide have diabetes, of which 90% suffer from type 2 diabetes mellitus. Typical long-term complications include development of neuropathy, retinopathy, nephropathy, generalized degenerative changes in large and small blood vessels and increased susceptibility to infection. Since individuals with type 2 diabetes still have a residual amount of insulin available in contrast to type 1 diabetic individuals, who completely lack the production of insulin, type 2 diabetes only surfaces gradually and is often diagnosed several years after onset, once complications have already arisen.

Insulin resistance occurs in 25% of non-diabetic, non-obese, apparently healthy individuals, and predisposes them to both diabetes and coronary artery disease. Hyperglycemia in type II diabetes is the result of both resistance to insulin in muscle and other key insulin target tissues, and decreased beta cell insulin secretion. Longitudinal studies of individuals with a strong family history of diabetes indicate that the insulin resistance precedes the secretory abnormalities. Prior to developing diabetes these individuals compensate for their insulin resistance by secreting extra insulin. Diabetes results when the compensatory hyperinsulinemia fails. The secretory deficiency of pancreatic beta cells then plays a major role in the severity of the diabetes.

Human insulin-dependent diabetes mellitus (IDDM) is a disease characterized by autoimmune destruction of the β cells in the pancreatic islets of Langerhans. An animal model for the disease is the non-obese diabetic (NOD) mouse, which develops autoimmunity. NOD mice spontaneously develop inflammation of the islets and destruction of the β cells, which leads to hyperglycemia and overt diabetes. Both CD4+ and CD8+ T cells are believed to be required for diabetes to develop: CD4+ T cells appear to be required for initiation of insulitis, cytokine-mediated destruction of β cells, and probably for activation of CD8+ T cells. The CD8+ T cells in turn mediate β cell destruction by cytotoxic effects such as release of granzymes, perforin, TNF α and IFN γ.

The depletion of β cells results in an inability to regulate levels of glucose in the blood. Overt diabetes occurs when the level of glucose in the blood rises above a specific level, usually about 250 mg/dl. In humans a long presymptomatic period precedes the onset of diabetes. During this period there is a gradual loss of pancreatic β cell function. The disease progression may be monitored in individuals diagnosed by family history and genetic analysis as being susceptible. The most important genetic effect is seen with genes of the major histocompatibility locus (IDDM1), although other loci, including the insulin gene region (IDDM2) also show linkage to the disease (see Davies et al, supra and Kennedy et al. (1995) Nature Genetics 9:293-298). Markers that may be evaluated during the presymptomatic stage are the presence of insulitis in the pancreas, the level and frequency of islet cell antibodies, islet cell surface antibodies, aberrant expression of Class II MHC molecules on pancreatic β cells, glucose concentration in the blood, and the plasma concentration of insulin. An increase in the number of T lymphocytes in the pancreas, islet cell antibodies and blood glucose is indicative of the disease, as is a decrease in insulin concentration. After the onset of overt diabetes, patients with residual β cell function, evidenced by the plasma persistence of insulin C-peptide, may also benefit from the subject treatment, to prevent further loss of function.

The subject therapy may be administered during the presymptomatic or preclinical stage of the disease, and in some cases during the symptomatic stage of the disease. Early treatment is preferable, in order to prevent the loss of function associated with inflammatory tissue damage. The presymptomatic, or preclinical stage will be defined as that period not later than when there is immune cell involvement at the site of disease, e.g. islets of Langerhans, synovial tissue, thyroid gland, etc., but the loss of function is not yet severe enough to produce the clinical symptoms indicative of overt disease, for example as evidenced by the presence of elevated numbers of T cells at the site of disease, the presence of T cells specific for autoantigens, the release of performs and granzymes at the site of disease, response to immunosuppressive therapy, etc.

By "effective amount" or "effective dose" is meant the amount of engineered MSC sufficient to produce a clinically beneficial result in the treatment of animals, preferably mammals, and more preferably humans.

Engineered MSC

Embodiments of the invention include MSC that have been engineered to express a CAR of the invention, which may be a CAR comprising an scFv that specifically binds to FRβ, particularly human FRβ; or may be a CAR that specifically binds to a non-endogenous antigenic moiety, e.g. FITC, which is typically administered in combination with a targeting antibody comprising the non-endogenous targeting moiety. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector or mRNA, has been introduced. Therefore, recombinant cells are distinguishable from naturally occurring cells which do not contain a recombinantly introduced nucleic acid. As discussed above, the engineered MSC can also comprise exogenous coding sequences for immunomodulatory proteins, e.g. one or both of IL-4 and IL-13.

The cells can be autologous cells, syngeneic cells, allogeneic cells and even in some cases, xenogeneic cells. In many situations, one may wish to be able to kill the engineered MSC. For this purpose, one can provide for the expression of certain gene products in which one can kill the modified cells under controlled conditions, such as inducible suicide genes.

In particular cases an individual is provided with therapeutic MSC engineered to comprise an FRβ specific CAR of the invention, where indirect binding engineered MSC are administered in combination with a targeting antibody. The cells may be delivered at the same time or at different times as another type of therapy. The cells may be delivered in the same or separate formulations as another type of therapy. The cells may be provided to the individual in separate delivery routes as another type of therapy. The cells may be delivered by injection at a lesion site, i.v., i.m., i.p., etc. Routine delivery routes for such compositions are known in the art.

Expression vectors that encode the CAR of the invention can be introduced as one or more DNA molecules or constructs, where there may be at least one marker that will allow for selection of host cells that contain the construct(s). The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. The construct(s) once completed and demonstrated to have the appropriate sequences may then be introduced into the CTL by any convenient means. The constructs may be integrated and packaged into non-replicating, defective viral genomes like Adenovirus, Adeno-associated virus (AAV), or Herpes simplex virus (HSV) or others, including retroviral vectors or lentiviral vectors, for infection or transduction into cells. The constructs may include viral sequences for transfection, if desired. Alternatively, the construct may be introduced by fusion, electroporation, biolistics, transfection, lipofection, or the like. The host cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In some embodiments AAV, retroviral or lentiviral vectors are used to deliver the CAR of the invention to MSC. Adeno associated virus (AAV) is an attractive vector system for use in the cells of the present invention as it has a high frequency of integration and it can infect nondividing cells, thus making it useful for delivery of genes into mammalian cells, for example, in tissue culture or in vivo. AAV has a broad host range for infectivity. Details concerning the generation and use of rAAV vectors are described in U.S. Pat. Nos. 5,139,941 and 4,797,368, each incorporated herein by reference.

Retroviruses are useful as delivery vectors because of their ability to integrate their genes into the host genome, transferring a large amount of foreign genetic material, infecting a broad spectrum of species and cell types and of being packaged in special cell lines.

Lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2 and the Simian Immunodeficiency Virus: SIV. Recombinant lentiviral vectors are capable of infecting non-dividing cells and can be used for both in vivo and ex vivo gene transfer and expression of nucleic acid sequences. In some embodiments, the lentiviral vector is a third-generation vector (see, for example, Dull et al. (1998) J Virol. 72(11):8463-71). Such vectors are commercially available. 2nd generation lentiviral plasmids utilize the viral LTR promoter for gene expression, whereas 3rd-generation transfer vectors utilize a hybrid LTR promoter, see, for example Addgene for suitable vectors.

The cells may be administered as desired. Depending upon the response desired, the manner of administration, the life of the cells, the number of cells present, various protocols may be employed. The number of administrations will depend upon the factors described above at least in part.

Methods of Treatment

The MSC that have been modified with the construct(s) are grown in culture under selective conditions and cells that are selected as having the construct may be expanded and further analyzed, using, for example; the polymerase chain reaction for determining the presence of the construct in the host cells. Once the modified host cells have been identified, they may then be used as planned, e.g. expanded in culture or introduced into a host organism.

Depending upon the nature of the cells, the cells may be introduced into a host organism, e.g. a mammal, including humans, in a wide variety of ways. The cells may be introduced at the site of the inflammatory lesion, e.g. at the pancreatic islets. The dose of cells may be up to about $10^3$/kg body weight, $10^4$/kg body weight, $10^5$/kg body weight, $10^6$/kg body weight, $10^7$/kg body weight, or more.

The engineered cells may be administered in any physiologically acceptable excipient (e.g., William's E medium), where the cells may find an appropriate site for survival and function. The cells may be introduced to the subject (i.e., administered into the individual) via any of the following routes: parenteral, intraperitoneal, subcutaneous, intravenous, intraocular, into spinal fluid, and the like. The cells may be introduced by injection (e.g., direct local injection), catheter, or the like. Examples of methods for local delivery include, e.g., bolus injection, e.g. by a syringe, e.g., into a joint or organ; e.g., by continuous infusion, e.g. by cannulation, or by implanting a device upon which the cells have been reversibly affixed.

Targeting antibodies can be administered to a subject prior to, or concurrent with, or after administration of CAR expressing MSC. The targeting antibodies bind to target cells in the subject, e.g. sites of inflammatory lesions. The targeting antibodies may be formulated for administered to a subject using techniques known to the skilled artisan. Formulations of the tagged proteins may include pharmaceutically acceptable excipient(s). Excipients included in the formulations will have different purposes depending, for example, on the nature of the tag, the protein, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents.

A formulation of targeting antibodies may include one type of targeting antibody, or more than one, such as two, three, four, five, six or more types of targeting antibodies. The different types of targeting antibodies can vary based on the identity of the antigenic moiety, the identity of the antibody, or both.

The targeting antibodies may be administered to a subject using modes and techniques known to the skilled artisan. Exemplary modes include, but are not limited to, intravenous, intraperitoneal, and intratumoral injection. Other modes include, without limitation, intradermal, subcutaneous (s.c., s.q., sub-Q, Hypo), intramuscular (i.m.), intraarterial, intramedullary, intracardiac, intra-articular (joint), intrasynovial (joint fluid area), intracranial, intraspinal, and intrathecal (spinal fluids). Any known device useful for parenteral injection or infusion of the formulations can be used to effect such administration.

Formulations comprising the targeting antibodies are administered to a subject in an amount which is effective for targeting. In general, formulations comprising at least about 0.1 mg/kg to about 100 mg/kg body weight of the tagged proteins are administered to a subject in need of treatment. In most cases, the dosage is from about 1 mg/kg to about 10 mg/kg body weight of the tagged proteins daily, taking into account the routes of administration, symptoms, etc.

In some embodiments, the subject has been diagnosed with T1D or IDDM, or pre-IDDM or pre-T1D prior to administration of the engineered MSC. In some embodiments the patient has been transplanted with pancreatic islets. One of skill in the art can determine the patients who would potentially benefit from a therapeutic agent that would reduce or prevent the development of overt diabetes. One of skill in the art can determine the therapeutically effective amount of the composition to be administered to a subject based upon several considerations, such as local effects, pharmacodynamics, absorption, metabolism, method of delivery, age, weight, disease severity and response to the therapy.

An improvement in diabetic parameters may be any observable or measurable improvement. Thus, one of skill in the art realizes that a treatment may improve the patient or subject's condition, but may not be a complete cure of the disease. In certain aspects, the composition is administered in an effective amount to decrease, reduce, inhibit or abrogate levels of immune response from the donor's cells, tissue and/or organ against the host's tissues.

An improvement in pancreatic inflammation, e.g. IDDM, is also any observable or measurable improvement. Thus, one of skill in the art realizes that a treatment may improve the patient or subject's condition, but may not be a complete cure of the disease. In certain aspects, the composition is administered in an effective amount to decrease, reduce, inhibit or abrogate levels of immune response from the donor's cells, tissue and/or organ against the host's tissues.

Efficacy may be monitored in a patient during treatment, e.g. by monitoring weight for a reduction in obesity, where weight loss of at least about 5%, at least about 10%, at least about 15% or more can indicate successful treatment. Measurement of insulin sensitivity is another relevant marker for monitoring efficacy, where an increase in M value may be at least about 10%, at least about 25%, at least about 50% or more with successful therapy, for example normal values for a non-insulin resistant subject may be at least about 8, at least about 9, at least 10 or higher.

In an embodiment of the present invention, the engineered MSC composition is administered in an effective amount to decrease, reduce, inhibit or abrogate inflammation of the pancreas and toxicity related to standard therapy, in combination with an effective dose of targeting antibodies. The amount of antibody in the composition may vary from about 1 ng to about 1 g, more preferably, 0.1 mg to about 100 mg.

Treatment regimens may vary as well, and often depend on the health and age of the patient. Certain types of disease will require more aggressive treatment, while at the same time, certain patients cannot tolerate more taxing regimens. The clinician will be best suited to make such decisions based on the known efficacy and toxicity (if any) of the therapeutic formulations.

In specific embodiments, the composition is given in a single dose or multiple doses. The single dose may be administered daily, or multiple times a day, or multiple times a week, or monthly or multiple times a month. A series of doses may be administered daily, or multiple times a day, weekly, or multiple times a week, or monthly, or multiple times a month.

The improvement is any observable or measurable improvement. Thus, one of skill in the art realizes that a treatment may improve the patient or subject's condition, but may not be a complete cure of the disease. In certain aspects, the composition is administered in an effective amount to decrease, reduce, inhibit or abrogate levels of an immune response against the recipient.

In order to increase the effectiveness of oral administration of the composition of the present invention, these compositions may be combined with conventional therapy.

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment. To prepare pharmaceutical compositions, an effective amount of the antibody may be dissolved or dispersed in a pharmaceutically acceptable carrier or aqueous medium. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with various of the other ingredients enumerated above, as required, followed by filtered sterilization.

Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose.

These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The targeting antibodies may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Any of the compositions described herein may be comprised in a kit. In a non-limiting example, one or more cells for use in cell therapy and/or the reagents to generate one or more cells for use in cell therapy that harbors recombinant expression vectors may be comprised in a kit. The kit components are provided in suitable container means. Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow molded plastic containers into which the desired vials are retained.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

All references cited in this specification are hereby incorporated by reference in their entirety. The following examples are solely for the purpose of illustrating one embodiment of the invention.

The invention will further be illustrated in view of the following figures and example.

EXPERIMENTAL

Example 1

Engineered Mesenchymal Stem Cell Therapy to Promote Immunological Tolerance to Pancreatic Islets Engineered mesenchymal stem cells (MSCs) targeting inflammatory macrophages are generated by applying chimeric antigen receptor (CAR) technology for the treatment of type 1 diabetes (T1D). With a growing incidence, particularly in pediatric populations, T1D affects nearly 1:300 in the U.S. An economically viable treatment is provided. MSC-based therapy is currently undergoing clinical trials for transplantation tolerance and the treatment of immunological diseases, because of MSCs' ability for both tissue regeneration and modulatory capabilities on innate and adaptive immune responses. Targeting MSCs to pancreatic islets can help both islet transplantation and the treatment of new onset T1D. Macrophage-mediated pro-inflammatory response during the T1D progression or following islet transplantation is associated with immunological rejection of islets.

We investigated the therapeutic application of the anti-inflammatory cytokine IL-4 in inflammatory diseases; IL-4 polarizes inflammatory M1 macrophages into anti-inflammatory, tissue reparative M2 macrophages. We have developed IL-4 secreting MSCs by genomic editing, and demonstrated enhanced immunomodulation on macrophage-mediated proinflammatory responses compared to parental unmodified MSC delivery. Modulation of macrophage polarization can alleviate the adverse inflammatory response, and also enhance angiogenesis and tissue regeneration via the crosstalk between MSCs and macrophages. However, the clinical application of MSC-based therapy is currently limited to local infusion due to lack of specific targeting mechanisms during systemic administration.

Figure 1A:
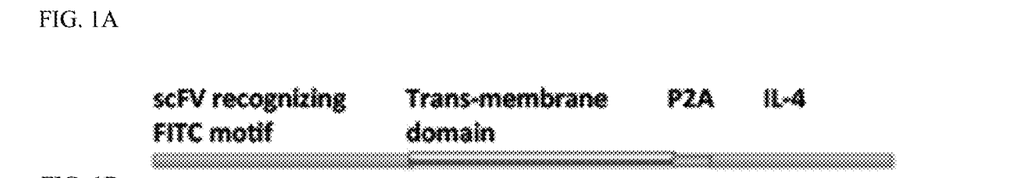
(FIG. 1A) Construction design of iCAR-MSC with IL-4 secretion.
Figure 1B:
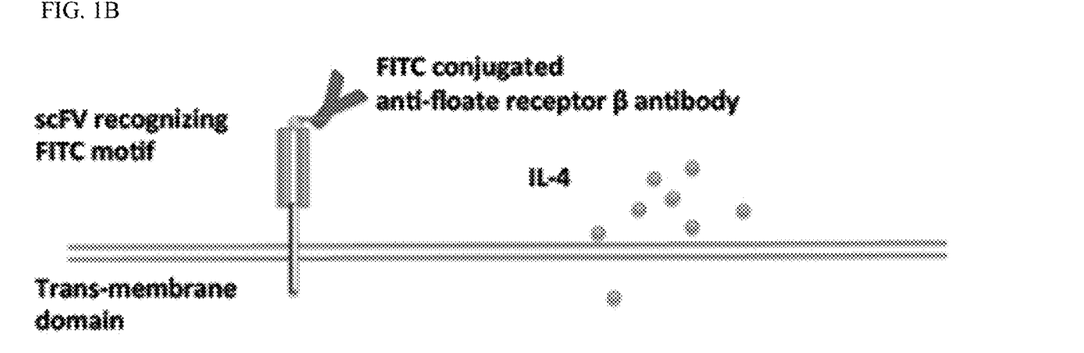
(FIG. 1B) The anti-Folate receptor β antibody is conjugated with FITC motif, which is recognized by scFV expressed by transduced MSCs. The linkage peptide P2A will be cleaved and the IL-4 will be secreted.
Figure 2A:
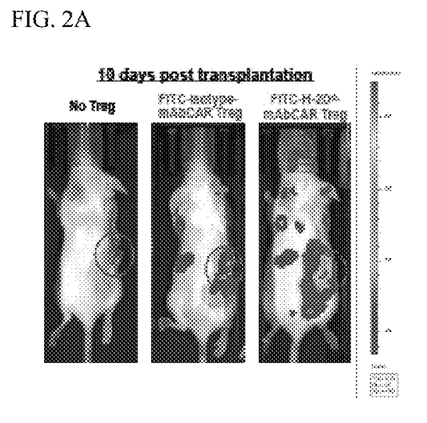
FIG. 2A-2B. Localization of cells to targeted sites.
Figure 2B:
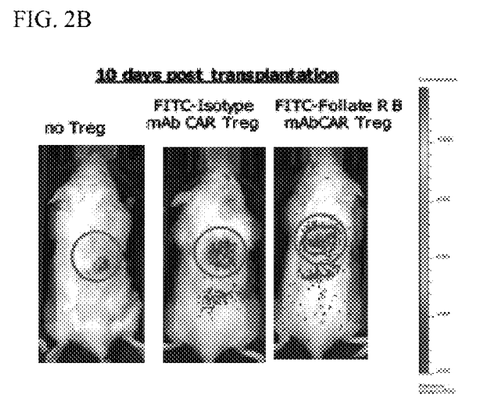

Chimeric antigen receptor T cells (CAR T cell) have been developed that recognize FITC, a nonendogenous, fluorescent dye used to tag antibodies. These 'interposed' CAR-T (iCAR-T) cells activate when they recognize the FITC-tag of an antibody that can be flexibly targeted towards any number of endogenous epitopes. The same approach is applied to targeting MSCs (see FIGS. 1 and 2).

Novel engineered MSCs are generated that will target M1 macrophages systemically, and polarize the cells into anti-inflammatory M2 phenotypes. Folate receptor β is an ideal target for M1 macrophages. Expression of folate receptor β has been shown in pro-inflammatory M1 macrophages. Systemic delivery of the fluorescent probes targeting folate receptor β has been co-localized with M1 macrophages, and has demonstrated the specific interaction and binding in vivo. Over-expressing IL-4 MSCs are used to a) create the iCARMSC specifically towards inflammatory M1 macrophages by targeting folate receptor β, and b) secrete the immune-modulating cytokine IL-4 to mitigate the inflammatory response after islet transplantation (FIG. 1). The iCAR-MSC study directly targets islet transplantation and T1D, which could benefit 40,000 patients annually.

There is no standard immune suppression to treat new onset T1D. Combination immunosuppressive therapy is the current standard treatment for post-transplantation pancreatic islet cell rejection. However, these treatments are associated with significant adverse effects including risk of sepsis, fatigue, and other systemic sequela, as well as impaired islet cell function. Cell-based immunomodulating therapy has great potential to prevent rejection with minimal morbidity. MSC-based cell therapy is highlighted by 1) the feasibility of allogeneic cell transplantation; 2) abundant cell sources (bone marrow and adipose tissue) and capability of in vitro expansion; and 3) the tissue regeneration potential.

The efficiency of systemic delivery of MSCs to inflamed islets in general is limited by the lack of specific targeting mechanisms. In addition, the immunomodulatory capabilities of MSCs on the innate immune response in the absence of pathogen-associated molecule patterns remain unclear. The novel strategy of iCAR-MSCs can recognize inflammatory M1 macrophages and target the islet cell transplantation site systemically, and subsequently polarize the local tissue environment into a biologic milieu characterized by anti-inflammatory, tissue reparative phenotypes.

Generation of Engineered Mesenchymal Stem Cells Targeting Inflammatory M1 Macrophages.

MSCs are generated by RNA electroporation to express iCARs that recognize anti-FITC motif. IL-4 expression is also transduced with the P2A linkage peptide (FIG. 1A). FITC-conjugated anti-folate receptor β antibody (FIG. 1B) is used to couple with iCAR-MSC. Folate receptor β is specifically expressed on inflammatory M1 macrophages. The coating of iCAR-MSC with FITC-conjugated antibody and the IL-4 secretion is examined in vitro.

Systemic Trafficking of Folate Receptor β Recognizing iCAR-MSCs in an Inflammatory Disease Model with Islet Cell Transplantation.

MSCs isolated from the luciferase expressing transgenic mice are transduced with iCARs targeting folate receptor β. In an established murine model of allogeneic islet cell transplantation, iCAR-MSC are delivered systemically, and the luciferase signaling is determined by the in vivo imaging system (IVIS).

Therapeutic Efficacy of iCAR-MSCs in Modulating the Islet Transplantation-Induced Inflammation in Murine Models.

The generated IL-4 secreting iCAR-MSC are systemically delivered into islet cell-transplanted mice. M1/M2 polarized macrophage fluorescent probes are used to examine the inflammatory status modulated by the iCARMSC at the islet transplantation site. The functions of transplanted islet cells is evaluated by insulin secretion and glucose tolerance test.

A human cell model of iCAR-MSC conjugated with anti-human folate receptor antibody is generated with the human folate receptor β scFv construct.

Anti-FITC iCAR T cells have been generated and demonstrated efficient in vivo targeting effect to the desired location in the murine model. CAR MSC directed to the islet graft ($H-2D_d$) show enhanced localization to the islet allograft (FIG. 2A). CAR-Treg directed to a skin graft (Folate receptor β) show enhanced localization to the skin allograft (FIG. 2B).

Figure 3:
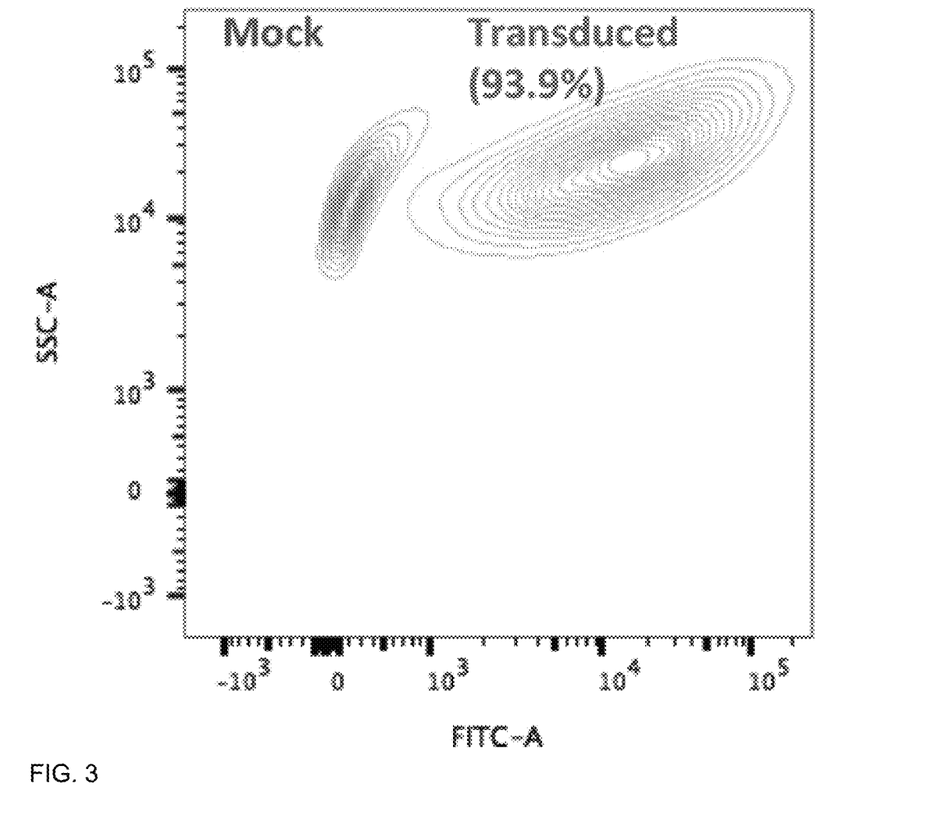
FIG. 3. Electroporation of murine MSC with GFP reporter RNA.

We have achieved in vitro expansion of murine MSCs and have transduced them with RNA encoded GFP gene expression (FIG. 3). Murine MSCs were isolated from femoral and tibial bone marrow using established protocols. Immunophenotypes and multi-lineage differentiation abilities of the isolated MSCs were characterized. The GFP reporter construct was transduced into MSCs by electroporation (Lonza). GFP+ MSCs were characterized by flow cytometry. We also generated genetically modified IL-4 secreting MSCs and demonstrated that IL-4 secretion significantly enhanced macrophage polarization into anti-inflammatory M2 phenotypes.

Example 2

Figure 4:
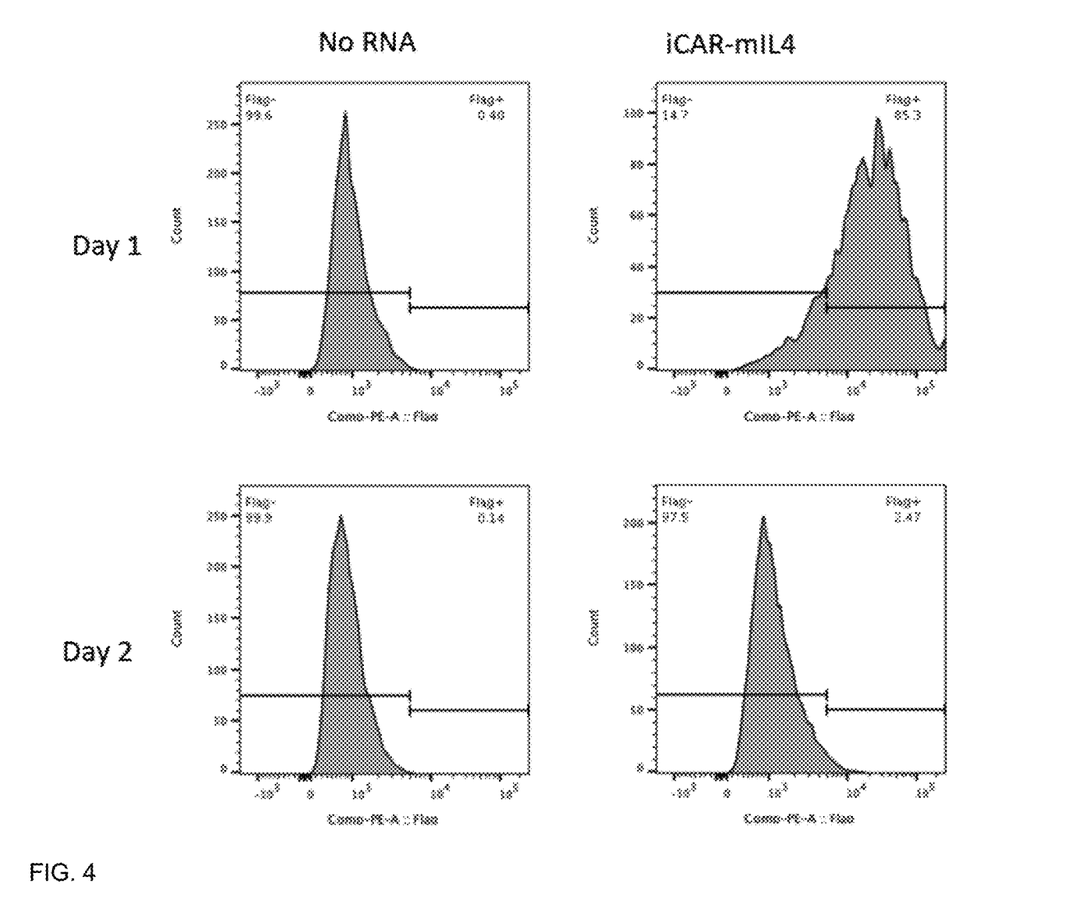
FIG. 4. Expression of iCAR receptor and the conjugation of anti-folate receptor β on the transfected iCAR-MSC. Anti-mouse folate receptor β antibody was conjugated to the iCAR-MSC (right) or mock-transfected control (left) at day 1 and day 2 post-electroporation. The successful conjugation was determined by FACS.

Mouse MSC were electroporated with mRNA encoding an iCAR receptor as shown in FIG. 1. The iCAR receptor includes an scFv specific for FITC. To coat the MSC with antibodies specific for anti-mouse folate receptor β antibody, the electroporated cells were cultured for 1 or 2 days post electroporation, then resuspended in a solution containing FITC conjugated anti-mouse folate receptor β antibody. The unbound antibody was washed off, the cells analyzed by flow cytometry. The results are shown in FIG. 4.

Figure 5:
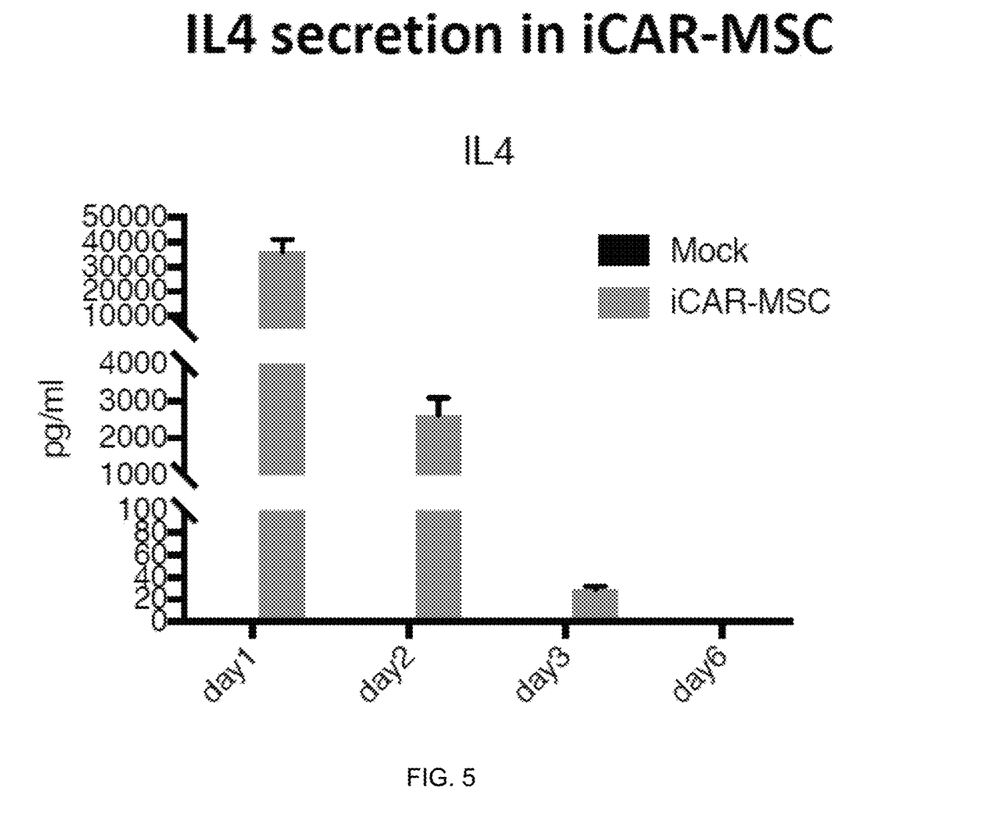
Figure 6:
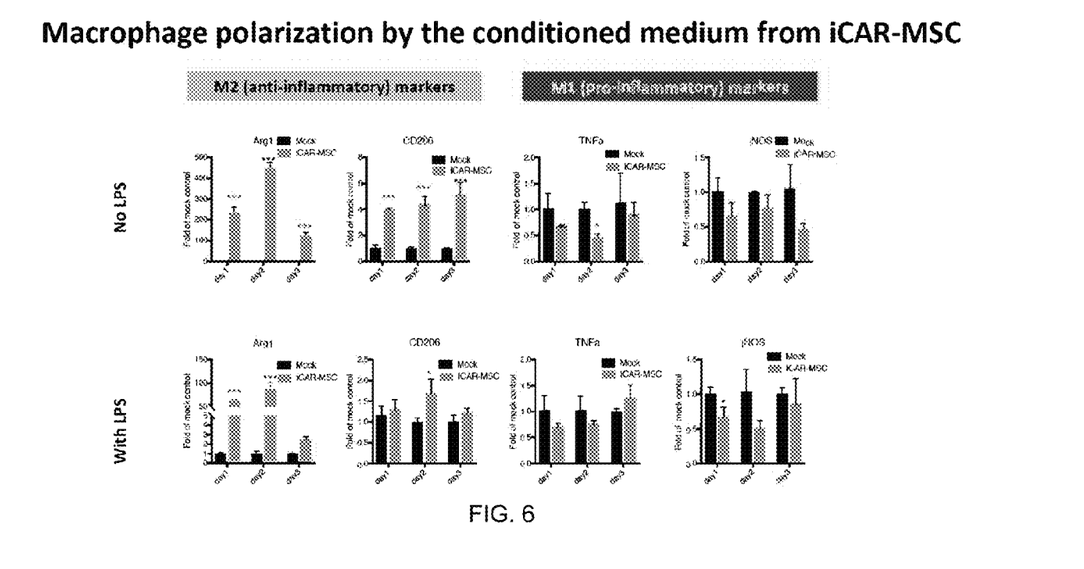

$6\times10^6$ of iCAR-MSC and a mock-transfected control were seeded into T175 culture flasks after electroporation. The supernatant was collected at day 1, 2, 3, and 6 post-electroporation, and the IL4 level was quantified by ELISA (eBioscience), results shown in FIG. 5. The conditioned medium from different time points after electroporation was used to treat mouse macrophages in the absence or presence of 100 ng/ml LPS (M1 stimulator). After one day, the macrophage cellular RNA was harvested from the macrophages and analyzed for the presence of anti-inflammatory (M2, Arginase 1/CD206) and pro-inflammatory (M1, TNFα/ iNOS) markers by quantitative PCR using Taqman system (Applied Biosystems). Data is shown in FIG. 6.

What is claimed is:

1. A method for treating an inflammatory condition in a subject in need thereof, comprising administering to said subject:
    an effective dose of mesenchymal stromal cells (MSC) engineered to express a chimeric antigen receptor (iCAR) that specifically binds folate receptor beta (FRβ); wherein the MSC has been further engineered to express an anti-inflammatory cytokine
    wherein inflammation is decreased at the targeted site.

2. The method of claim 1, wherein the cytokine is one or both of IL4 and IL-13.

3. The method of claim 1, wherein the cytokine is expressed as a fusion protein linked to the iCAR by a cleavable peptide.

4. The method of claim 1, wherein the cytokine is expressed independently of the CAR.

5. The method of claim 4, wherein cytokine expression is regulated.

6. The method of claim 1, wherein the iCAR directly binds to FRβ.

7. The method of claim 1, wherein the MSC cells are autologous.

8. The method of claim 1, wherein the MSC cells are allogeneic.

9. The method of claim 7, wherein the MSC are engineered and expanded in culture.

10. The method of claim 1, wherein the subject is a human.

11. The method of claim 1, where the inflammatory condition is diabetes.

12. A method for treating an inflammatory condition in a subject in need thereof, comprising administering to said subject:
    an effective dose of mesenchymal stromal cells (MSC) engineered to express a chimeric antigen receptor (iCAR) that specifically binds folate receptor beta (FRβ); administered in combination with an effective dose of targeting antibodies, which antibodies (i) bind to FRβ and (ii) are labeled with the non-endogenous antigenic moiety.

* * * * *